United States Patent [19]

Cattani et al.

[11] 4,448,771

[45] May 15, 1984

[54] FRUCTOSE-1,6-DIPHOSPHATE PREPARATION HAVING PROTECTIVE ACTION OF ERYTHROCYTE MEMBRANE IN PATIENTS UNDERGOING EXTRACORPOREAL CIRCULATION

[75] Inventors: Luciano Cattani, Bologna; Renato Costrini, Rome, both of Italy

[73] Assignee: Biomedica Foscama Industria Chimico-Farmaceutica S.p.A., Rome, Italy

[21] Appl. No.: 242,128

[22] Filed: Mar. 9, 1981

[30] Foreign Application Priority Data

Mar. 12, 1980 [IT] Italy ................. 48137 A/80

[51] Int. Cl.³ .................................... A61K 31/70
[52] U.S. Cl. .................................... 424/180
[58] Field of Search .................... 424/180; 536/117

[56] References Cited

PUBLICATIONS

Chemical Abstracts, vol. 93, 1980, p. 86, (Costrini et al.), (896s).
Chemical Abstracts, vol. 71, 1969, p. 275, 84553j.
Chemical Abstracts, vol. 70, 1969, p. 393, 88201v.
Chemical Abstracts, vol. 91, 1979, p. 289, (Higashi et al.), (170818u).
Costrini et al., IRCS Clinical Medicine, vol. 8, pp. 257–258 (1980).

*Primary Examiner*—Jerome D. Goldberg
*Attorney, Agent, or Firm*—Michael J. Striker

[57] ABSTRACT

A preparation of fructose-1,6-diphosphate sodium salt made of a 10% solution in apyrogenic bidistilled water, characterized by protective activity of erythrocyte membrane.

1 Claim, No Drawings

FRUCTOSE-1,6-DIPHOSPHATE PREPARATION HAVING PROTECTIVE ACTION OF ERYTHROCYTE MEMBRANE IN PATIENTS UNDERGOING EXTRACORPOREAL CIRCULATION

The object of the present invention is a fructose-1,6-diphosphate preparation (FDP) having protective action of erythrocyte membrane in patients undergoing extracorporeal circulation. More particularly the invention concerns a preparation of fructose-1,6-diphosphate sodium salt for intravenous administration which remarkably inhibits the erythrocyte fragility usually brought about by extracorporeal circulation (ECC).

Experimentally it is known that extracorporeal circulation (ECC) needed in several cardiosurgery operations, produces considerable mechanical and chemical damages of erythrocyte membrane (Bernstein, E. F. et al. (1967) Am. J. Surg. 114, 126) revealed by intravascular haemolysis and postperfusional anaemia, due to shortening of red corpuscles average life. The retarded effect is greater than the immediate one and can be estimated by extravascular haemolysis directly depending on the intravascular one and completely absent if this is lacking (Bernstein, E. F. et al. (1967) Circulation 45 (suppl.1), 226 and Wallace, H. W. and Coburn, R. F. (1974) J. Thorac. Cardiovasc. Surg. 68, 792).

The erythrocyte membrane alterations, brought about by ECC, join metabolism and red corpuscle functions alterations and particularly the oxyphoretic one (Glynn, M. F. X. and Cornhill, F. (1965) Can. J. Surg. 18, 73) with following tissue oxygenation damage.

As it is evident, because of this, the increase of erythrocyte fragility brough about by ECC contributes to worsen patients' operating and post-operating course.

In particular it has to be observed that up today no therapeutical measure able to prevent this serious drawback has been found.

The present invention offers a surprising solution to the problem of finding means apt to reduce damages brought about now by ECC on erythrocyte membrane substantially, thus protecting patients from following intravascular haemolysis and post-perfusional anaemia, using as therapeutical medium the fructose-1,6-diphosphate sodium salt, product well known in other fields of pharmacology for its activity in cardiopathies, hepathities, cirroses, toxemiae, diabetic dismetabolic conditions, etc. to be administered intravenously with dosages greater than those prescribed in the cited applications known up today.

Therefore it is evident the great advantage offered by the preparation of the present invention in all the cases where the use of extracorporeal circulation (ECC) is needed, to attenuate the principal damages caused by this technique widely used in the normal practice of cardiosurgery substantially.

Therefore it is the specific object of this invention a preparation of fructose-1,6-diphosphate sodium salt made of a 10% solution in apyrogenic bidistilled water to be administered intravenously in dose not smaller than 2,5 ml/Kg body weight, to patients undergoing extracorporeal circulation.

This new use of sodium salt fructose-1,6-diphosphate in case of erythrocyte fragility brought about by ECC, is based on the existence of a FDP activity, not known previously, which has been checked and experimentally controlled in clinical tests (Istituto di Anestesia e Rianimazione dell'Università di Roma).

In this respect the results of a series of clinical tests carried out on patients undergoing ECC are reported hereinbelow.

CONTROLLED CLINICAL RESEARCH 39 patients undergoing cardiosurgical operations in ECC were divided "at random" in two groups. Group A included 7 men and 13 women from 8 to 58 years old treated with 2,50 ml/kg of a solution at 10% of FDP ("ESOFOSFINA" phlebo).

Group B included 9 men and 10 women from 11 to 55 years old treated with the same amount of physiological solution.

Both treatment were carried out intravenously before the beginning of anaesthesia in 10–15 min.

Two blood abstraction were made on each patient: one (A) before the treatment, and the other (d) an hour after the beginning of ECC.

The extravascular haemolysis of the abstracted blood samples has been measured after incubation in a NaCl solution buffered at pH 7.4 according to the method of "erythrocyte osmotic fragility test after incubation" described by Nelson.

In order to lessen the bacterial infection risks, the incubation temperature has been modified to 22° C.

For each blood abstraction 10 test-tubes were prepared, mixing 5 ml solution at 0.756% in NaCl solution (buffered with 0.123% of $Na_2HPO_4$ and 0.022% of $NaH_2.2H_2O$) with 0.05 ml of heparinized blood. The incubation time varies for each of them from 1 to 10 days and at the end of incubation the percentage of haemolysis according to the above mentioned methods. Another test-tube containing distilled water has been used to ascertain the haemoglobin released by total haemolysis from the same quantity of blood. For these two treatments the difference between the percentage of haemolysis after treatment and that before treatment ($\Delta$-FDP and $\Delta$ Physiologic) have been estimated. For each incubation day the statistic meaning of $\Delta$-FDP (A) average value and that of $\Delta$ Physiologic (B) average value, has been controlled by Student's t test for coupled data, and the statistic datum of A-B difference by Student's t test for uncoupled data.

The results are reported in the hereinbelow table.

TABLE

Variations of percentage values of extravascular haemolysis after treatment with FDP or Physiologic after 1 hour of ECC. For abbreviations see the text.

| Incubation day | Average Value ± SEM of $\Delta$ FDP (A) | p* < | Average Value ± SEM of $\Delta$ Physiologic (B) | p* < | A-B | p** < |
|---|---|---|---|---|---|---|
| 1st | −0.076 ± 0.148 | ns | +0.384 ± 0.110 | .01 | −0.150 | .05 |
| 2nd | −0.737 ± 0.469 | ns | +0.324 ± 0.132 | .05 | −1.061 | .05 |
| 3rd | −1.911 ± 0.991 | ns | +0.746 ± 0.185 | .01 | −2.657 | .05 |
| 4th | −1.330 ± 0.894 | ns | +3.518 ± 1.075 | .01 | −4.848 | .01 |
| 5th | −2.064 ± 1.266 | ns | +3.139 ± 0.738 | .001 | −5.203 | .01 |
| 6th | −1.899 ± 1.040 | ns | +2.954 ± 0.644 | .001 | −4.854 | .001 |

TABLE-continued

Variations of percentage values of extravascular haemolysis after treatment with FDP or Physiologic after 1 hour of ECC. For abbreviations see the text.

| Incubation day | Average Value ± SEM of Δ FDP (A) | p* < | Average Value ± SEM of Δ Physiologic (B) | p* < | A-B | p** < |
|---|---|---|---|---|---|---|
| 7th | −1.527 ± 0.855 | ns | +2.791 ± 0.750 | .01 | −4.317 | .001 |
| 8th | −1.416 ± 0.712 | ns | +2.444 ± 0.808 | .01 | −3.860 | .01 |
| 9th | −3.124 ± 1.406 | .05 | +2.705 ± 0.936 | .02 | −5.830 | .01 |
| 10th | −2.536 ± 0.935 | .025 | +2.493 ± 0.707 | .01 | −5.029 | .001 |

*Student's t test for coupled data
**Student's t test for uncoupled data

It can be observed that in the blood abstracted after treatment with physiologic solution and after about one hour of ECC, the extravascular haemolysis has augmented statistically as concerns the basic values (p) in all the days of incubation.

On the other hand in the blood abstracted after treatment with the product of the invention and after one hour of ECC, the extravascular haemolysis shows a statistically significant decrease on 9th and 10th day as concerns the basic values (p).

The comparison between the two treatments (A-B) shows that FDP secures longer average erythrocitary life, as to the control treatment.

These results show the effectiveness of FDP ("ESAFOSFINA" phlebo) in preventing the damage brought about by ECC on erythrocytes.

The present invention has been described with particular reference to its specific embodiments, but it is intended that variations and modifications could be adopted without departing from the scope thereof.

What is claimed is:

1. A method of treatment for patients undergoing extracorporeal circulation, comprising intravenously administered to said patents the pharmaceutical preparation comprising a 10% solution of fructose-1,6-diphosphate sodium salt in apyrogenic bidistilled water in effective doses not less than 2.5 ml/kg of body weight.

* * * * *